United States Patent [19]

Milani et al.

[11] 4,420,482
[45] Dec. 13, 1983

[54] 1,4-BIS(ACETYLSALICYLOYLOXY)PIPERIZINE DERIVATIVES

[75] Inventors: Carlo Milani; Giovanni M. Carminati; Attilio Sovera, all of Milan, Italy

[73] Assignee: Selvi & C. S.p.A., Milan, Italy

[21] Appl. No.: 322,855

[22] Filed: Nov. 19, 1981

[30] Foreign Application Priority Data

Nov. 20, 1980 [IT] Italy ................................ 26131 A/80

[51] Int. Cl.³ .................... A61k 31/495; C07D 295/00
[52] U.S. Cl. .................................... 424/250; 544/383; 544/387; 544/398; 544/399
[58] Field of Search ...................... 544/399, 383, 387; 424/250

[56]  References Cited

U.S. PATENT DOCUMENTS

| 2,753,350 | 7/1956 | Hasselstrom | 544/383 |
| 3,966,735 | 6/1976 | Milkowski et al. | 544/399 |
| 3,980,643 | 9/1976 | Kato et al. | 544/399 |
| 4,346,231 | 8/1982 | Ponticello et al. | 544/383 |

OTHER PUBLICATIONS

Holmberg, et al., "Acta Chem. Scand.," vol. 33 (13), 1979 pp. 410-412.
Neelakantan, et al., "Tetrahedron," vol. 21, 1965, pp. 3531-3536.
Saigo, et al., "Bull. Chem. Soc. Japan," vol. 50 (7), 1977, pp. 1863-1866.
Brewster, et al., "J.A.C.S.," vol. 77, 1955, pp. 6214-6215.
Mukaiyama, et al., "Chem. Lett." Japan, 1976, pp. 13-14.
Buzas, et al., "C. R. Acad. Sc." vol. 256, 1963, pp. 1804-1806.
Mukaiyama, et al.," Chem. Lett.," Japan, 1975, pp. 1045-1048.

Primary Examiner—Donald G. Daus
Assistant Examiner—James H. Turnipseed
Attorney, Agent, or Firm—Walter H. Schneider

[57]  ABSTRACT

The present invention concerns compounds of the general formula

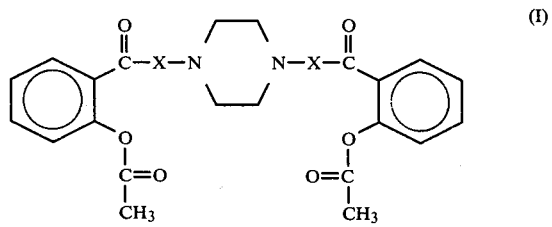

wherein X represents a direct linkage or a linear or branched oxyalkyl group containing one or more carbon atoms, as well as pharmaceutically acceptable salts of such compounds wherein X represents an oxyalkyl group, methods for their preparation by reaction of either piperazine or of its 1,4-bis-hydroxyalkyl derivatives with activated derivatives of acetylsalicylic acid such as halogenides, symmetric or mixed anhydrides, or with a haloalkylester of acetylsalicylic acid, and related pharmaceutical compositions having use as antipyretic, analgesic, anti-inflammatory and anti-histaminic agents.

9 Claims, No Drawings

1,4-BIS(ACETYLSALICYLOYLOXY)PIPERIZINE DERIVATIVES

The present invention concerns novel compounds of the general formula

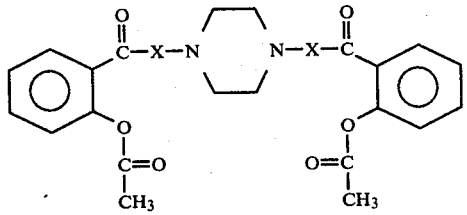
(I)

wherein X represents a direct linkage or a linear or branched oxyalkyl group containing one or more carbon atoms. The compounds of the formula (I), wherein X represents an oxyalkyl group, are characterised by a double basic function, and can therefore be salified with both organic and inorganic salts in order to provide mono- or di-salts with each acid. Not only acid salts but also basic and neutral salts can also be obtained when an inorganic or organic acid, which may for example be provided with a double acid function, is used.

The invention also concerns the use of one of the above mentioned compounds (or of its related salts), acting as active ingredient, for the formulation of antipyretic, analgesic, anti-inflammatory and anti-histaminic preparations. Some of the compounds with the formula (I) are endowed with pharmacological and therapeutic properties definitely much more favorable than those shown by acetylsalicylic acid.

The invention also provides a process for the preparation of a compound of the general formula (I) or of a pharmaceutically active salt according to the invention which comprises acylating one mole of piperazine or of a corresponding synmetrical 1,4-(dihydroxyalkyl) piperazine, or a salt thereof with two moles of acetylsalicylic acid or of an activated derivative thereof. According to an alternative procedure compounds of the general formula (I) wherein X represents a linear or branched oxyalkyl group containing one or more carbon atoms, or a pharmaceutically acceptable salt thereof can be prepared by a process which comprises reacting two moles of a haloalkyl ester of acetylsalicylic acid with one mole of piperazine.

Hence according to the present invention, the methods of synthesis by which the compounds of formula (I) can be obtained provide for two different routes.

(A) The first route consist generically of all the methods, duly described in the literature, of acylation of either simple piperazine (Formula III) or of a piperazine symmetric 1,4-bis(hydroxyalkyl) derivative (Formula IV) according to the hereinbelow reported Scheme A.

SCHEME A

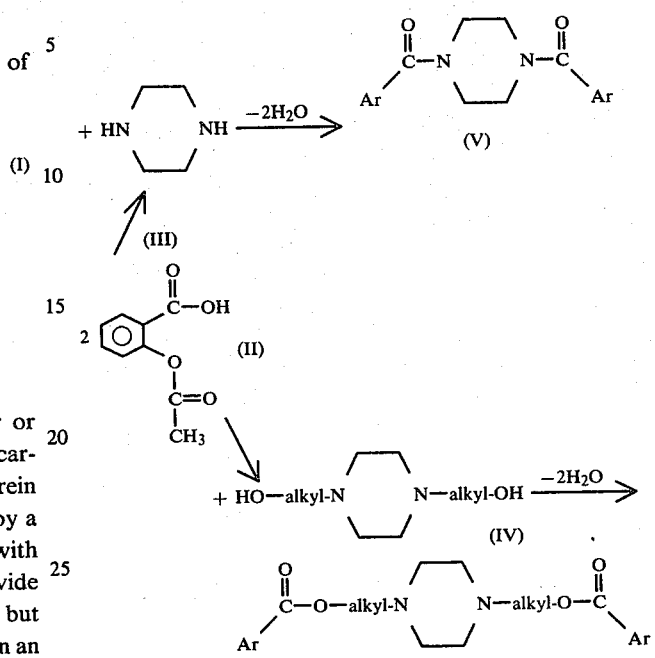

Both in Scheme A and in the hereinbelow reported Scheme B, Ar is always:

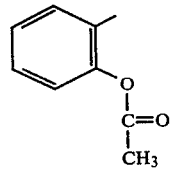

In the range of said methods of synthesis mention can be made, as example, of the reactions of activated derivatives of acetylsalicylic acid such as halogenides, symmetric anhydride or mixed anhydrides, for example mixed anhydrides of the general formula (VII),

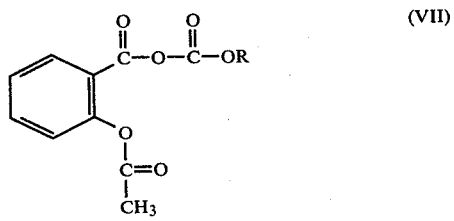
(VII)

with piperazine or with a piperazine 1,4-bis(hydroxyalkyl) derivative (IV).

Said methods, definitely not limitative to the effects of the synthesis of the compounds with formula (I), might also be extended to many other compounds such as, for example, the ones mentioned by: A. Busar et al, C. R. Acad Sc., 256, 1804 (1963)—S. Neelakuntar et al., Tetrahedron, 21, 3531 (1965)—J. H. Brewster, C. J. Ciotti, J. Am. Chem. Soc., 77,6214 (1955) K. Saige et al., Bull. Chem. Soc. Japan, 50, 1863 (1977) T. Mukayama et al., Chem. lett., 1975, 1045; 1976, 13 K. Holmberg, B. Harrsen, Acta Chem. Scand., (13),33, 410

(1979) and others, that confirm the essentials of the previously reported scheme.

(B) A second chemical route to obtain the compounds with formula (I) consists in preparing initially an ester (Formula VIII) of acetylsalicylic acid (Formula II) with a haloalcohol, and finally in causing the reaction of two equivalents of the haloalkylester with one equivalent of piperazine (Formula III) according to the hereinbelow reported Scheme B:

SCHEME B

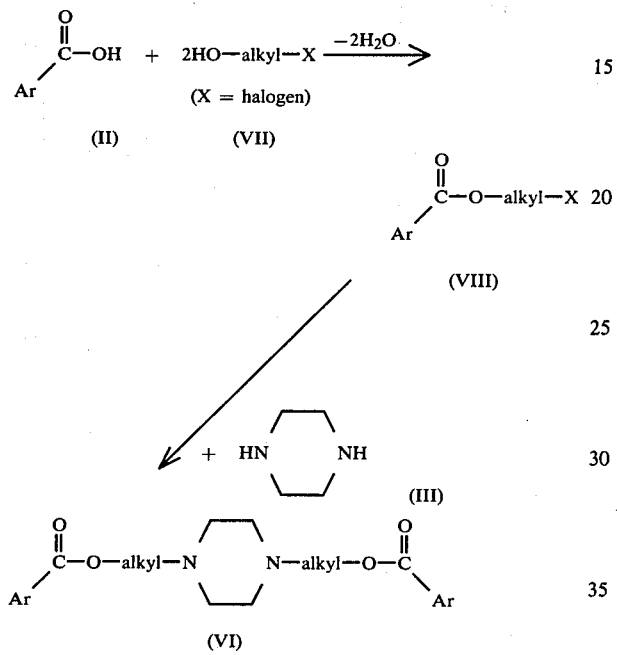

where Ar has the above mentioned significance. The compounds of formula (VIII) can be obtained by already well known methods while the last step, suited to obtain the compounds of Formula VI, consists in the condensation of two moles of the intermediate of formula VIII with one mole of piperazine anhydrous base (Formula III) in a suitable organic solvent, in the presence of a good acceptor of hydrohalogenic acid, and possibly in the presence of catalytic quantities of potassium iodide.

All the synthesized compounds of formula (I) have more or less marked antipyretic, analgesic, anti-inflammatory and anti-histaminic properties; among them, the compound of formula (I), where X=—O—CH$_2$—CH$_2$—, ie 1,4-BIS-[2-(ACETYLSALICYLOYLOXY)ETHYL] PIPERAZINE, that for brevity's sake shall be from now on defined with its code name "S.1528", proves particularly useful and effective because of its peculiar chemical, pharmacological, toxicological and therapeutic properties.

According to the present invention, S.1528 can be used therapeutically both as a free base and as a salt with pharmaceutically acceptable organic and inorganic salts. Pharmaceutical compositions, containing S.1528 and/or a related salt can be obtained both at the state of pure product and in the presence of a diluent or of a coating.

Such pharmaceutical compositions are suitable for use orally, rectally, parenterally and topically by the use of inert diluents, lubricants, emulsifying agents, dyes, aromatizers, excipients, etc., all compounds commonly used in pharmaceutical technology.

The new derivative of acetylsalicylic acid, ie S.1528, has been showing a quite mild toxicity associated with marked anti-inflammatory, antipyretic and analgesic activities as well as with an evident anti-histaminic activity. Moreover, unlike acetylsalicylic acid, the new compound appear to be entirely devoid of any gastric injuring effect. As can be seen from Table 1, the oral LD 50 in the mouse is approximately 2600 mg/kg; under the same experimental conditions, the LD 50 of acetylsalicylic acid is equivalent to 1000 mg/kg.

The anti-inflammatory activity of S.1528 was assessed in the paw carrageenin edema (220 Sprague Dawley male rats with a mean bodyweight of 150 g). As can be seen from Table 2, that reports the overall data obtained, equimolecular doses of S.1528 and acetylsalicylic acid show a quantitatively superimposable anti-inflammatory activity. It should be noted that, in the overall context of the present patent application the term "equimolecular doses" of S.1528 indicates all those doses that contain acetylsalicylic residues in a quantity equivalent to that of acetylsalicylic acid used as reference drug.

The analgesic activity of S.1528 was assessed on the sensitivity threshold of pain induced by a pressure exerted on a rat's paw inflamed by application of brewers' yeast (90 Sprague Dawley male rats with a mean bodyweight of 150 g). Also in this case, as can be seen from Table 3, equimolecular doses of S.1528 and acetylsalicylic acid exhibit quantitatively similar activity.

In hyperpyrexia, induced previously in the rat (Sprague Dawley, 80 males with a 200-g bodyweight) by an intramuscular administration of brewers' yeast, it was established that equimolecular doses of S.1528 and acetylsalicylic acid exert quite the same antipyretic activity; both compounds actually, when given at the dosage schedule of 236 mg/kg/os (in the case of S.1528) and 100 mg/kg/os (in the case of acetylsalicylic acid) induced a mean temperature decrease of one degree centigrade 1, 2 and 4 hours after the administration; when half dosage was given (ie, 118.5 and 75 mg/kg/os respectively) the mean decrease was 0.4 degrees centigrades for both compounds.

Table 4 points out the protective activity exerted by S.1528 versus the lethal shock induced in the guinea-pig by an inhaled histamine. It can be seen that, unlike S.1528, acetylsalicylic acid is entirely devoid of any antihistaminic activity. The dose of S.1528, that protects 50 percent of the guinea-pigs from the onset of a shock due to histamine, proved equivalent to 158 mg/kg.

Table 5, finally, reports the results of the investigations carried out in the rat with equimolecular doses of S.1528 and acetylsalicylic acid for the purpose of comparing the gastric ulcerogenic potency of the two anti-inflammatory agents: it results unquestionably from said Table that S.1528, unlike acetylsalicylic acid, exerts no gastric injuring effect, at least under the assessed experimental conditions. On the basis of the pharmacological investigations that have been carried out, it can be therefore concluded that, under equivalent molecular weights, the anti-inflammatory, antipyretic and analgesic activities of S.1528 do not differ quantitatively from those shown by acetylsalicylic acid.

Moreover all data reported on acute toxicity and activity show that the therapeutic index of S.1528, ie the ratio between the toxic dose and the active dose, proves more favorable than that of acetylsalicylic acid: actually it results to be 2600:158 (=16.45) in the case of S.1528, and 1000:100 (=10) in the case of acetylsalicylic acid.

S.1528, unlike acetylsalicylic acid, shows moreover an evident antihistaminic activity and does not show at least from the experimental standpoint, gastric injuring effects.

Both the pharmacological activities and the therapeutic indications, on the basis of which the patent for the compounds of formula (I) is applied for, are the anti-inflammatory, antipyretic, analgesic and antihistaminic activities for the symptomatic treatment of rheumatic and neuralgic syndromes.

The compound according to the invention can be administered through various routes, ie:

(a) oral: tablets, powder, granulates, syrups, solutions, emulsions, etc., of 0.4–0.8 g.
(b) parenteral: ampoules of 0.3–0.6 g.
(c) rectal: suppositories of 0.8–1.6 g.
(d) topical: creams; ointments, gels, etc. at a 5–10 percent dosage strength.

TABLE 1

Comparative oral acute toxicity, in the mouse, of S.1528 and acetylsalicylic acid

| Dose mg/kg/os | Mortality observed (7 days) with | |
|---|---|---|
| | S.1528 | Acetylsalicylic acid |
| 250 | — | 0 |
| 500 | — | 0 |
| 750 | 0/10 | 4/20 |
| 1000 | 0/10 | 10/20 |
| 1250 | — | 14/20 |
| 1500 | 0/20 | 20/20 |
| 1750 | 0/20 | 10/10 |
| 2000 | 4/20 | — |
| 2250 | 5/20 | — |
| 2500 | 8/20 | — |
| 2750 | 12/20 | — |
| 3000 | 16/20 | — |

TABLE 2

Comparative activity of equimolecular doses of S.1528 and of acetylsalicylic acid in the rat's paw carrageenin edema (overall 220 Sprague Dawley rats, 30 per group in three experiments)

| Compounds | Dose mg/kg/os | Comparative edema decrease in the various groups of untreated control animals | Statistical Significance P |
|---|---|---|---|
| Acetylsalicylic ac. | 55 | −28 | ns |
| S.1528 | 79 | −23 | ns |
| Acetylsalicylic ac. | 110 | −44 | <0.01 |
| S.1528 | 158 | −52 | <0.01 |
| Acetylsalicylic ac. | 221 | −79 | <0.01 |
| S.1528 | 317 | −83 | <0.01 |

TABLE 3

Analgesic activity of equimolecular doses of S.1528 and acetylsalicylic acid. Effect on the sensitivity threshold of pressure-induced pain on the paw inflamed by brewers' yeast (test of Randall and Selitto)

| Compound | Dose mg/kg/os | No. rats used (+) | Pain sensitivity threshold (g) of inflamed paw (++) | Threshold percent increase vs. controls |
|---|---|---|---|---|
| Peanuts oil (controls) | (10 ml/kg) | 30 | 90 ± 5.3 | — |
| Acetylsalicylic ac. | 110 | 30 | 122.6 ± 7.1 (+++) | 36.2 |
| S.1528 | 158 | 30 | 127.2 ± 6.3 (+++) | 41.3 |
| Acetylsalicylic ac. | 221 | 30 | 154.1 ± 5.7 (+++) | 71.2 |
| S.1528 | 317 | 30 | 152.2 ± 8.4 (+++) | 69.1 |

TABLE 3-continued

Analgesic activity of equimolecular doses of S.1528 and acetylsalicylic acid. Effect on the sensitivity threshold of pressure-induced pain on the paw inflamed by brewers' yeast (test of Randall and Selitto)

| Compound | Dose mg/kg/os | No. rats used (+) | Pain sensitivity threshold (g) of inflamed paw (++) | Threshold percent increase vs. controls |
|---|---|---|---|---|

(+) Mean data of three experiments
(++) Mean data emerged from the determinations made 1 and 2 hr after the administration of the investigational compounds
(+++) Statistically significant values ($P < 0.01$) versus the values provided by the control animals

TABLE 4

Protective activity of equimolecular doses of S.1528 and, for comparison, of acetylsalicylic acid on the lethal shock induced in the guinea-pig by inhaled histamine.

| Compound | Dose mg/kg/os | Route of admin. | No. guinea-pigs (+) | Time of resistance in min. | Protected animals | Percent Protection |
|---|---|---|---|---|---|---|
| Peanuts oil (controls) | (2 ml/kg) | orale | 84 | 62 ± 9.1 | 0 | — |
| Acetylsalicylic ac. | 110 | " | 20 | 66 ± 6.3 | 0 | — |
| S.1528 | 158 | " | 20 | 523 ± 45 | 12 | 60 |
| Acetylsalicylic ac. | 221 | " | 20 | 54 ± 11.3 | 0 | — |
| S.1528 | 317 | " | 20 | >720 | 20 | 100 |

(+) Mean data of three experiments.

TABLE 5

Ulcerogenic effect of equimolecular doses of S.1528 and reference acetylsalicylic acid, given orally to Sprague Dawley rats, M, mean weight = 200 g, fasted for 36 hours and killed 5 hours later.

| Treatment | Dose and route of admin. mg/kg | Incidence of gastric lesions (+) | Mean number of gastric ulcerations (mm) |
|---|---|---|---|
| Acetylsalicylic ac. | 110, os | 9/20 | 3,2 |
| S.1528 | 158, os | 0/20 | 0 |
| Acetylsalicylic ac. | 221, os | 16/20 | 2,9 |
| S.1528 | 317, os | 0/20 | 0 |
| Acetylsalicylic ac. | 221, i.p. | 14/20 | 4,1 |
| S.1528 | 317, i.p. | 0/20 | 0 |

(+) Number of animals with lesions versus the total of the animals treated.

EXAMPLE 1

(Scheme A—Product V)

1,4-bis (Acetylsalicyloyl)Piperazine (route: acid chloride)

Dissolve acetylsalicyloyl chloride (9.68 g, 0.049 moles) in an apolar solvent, represented preferably by toluene or benzene (100 ml). Shake vigorously. Into the round-bottom reaction flask add slowly a solution of anhydrous piperazine (2.1 g, 0.024 moles) and triethylamine (6.8 ml) in an apolar solvent, represented preferably by toluene or benzene (50 ml).

A precipitate, consisting of the desired product and triethylamine hydrochloride, is formed in the course of the reaction. As soon as dropping is terminated, shake for one additional hour, collect thereafter the solid and suspend it by agitation in 150 ml of water approximately.

Filter again the insoluble aliquot and crystallize from an alcohol, preferably ethanol, obtaining according to this procedure the analytically pure product (mp. 175°–177°, not corr.), TLC=Merck $F_{254}$ silica gel plates; eluent: anhydrous ethyl acetate, single spot Rf=0.38.

For $C_{22}H_{22}N_2O_6$ (410.41)—% found C 64.25; H 5.31; N 6.77; % calc. C 64.38; H 5.40; N 6.83.

I.R. (Nujol mull) — 1770 cm$^{-1}$ (stretching $-\overset{\overset{O}{\|}}{C}-O-$)

1630 cm$^{-1}$ (stretching $-\overset{\overset{O}{\|}}{C}-N\diagup\diagdown$)

N.M.R. (60 MHz; in DMSO d$^6$), δ relative to T.M.S.

2.23 (6H singlet) $CH_3-\overset{\overset{O}{\|}}{C}-O$;

3.0–3.8 (8H multiplet), piperazine H : 7.0–7.6 (8H, multiplet), aromatic H.

EXAMPLE 2

1,4-bis (Acetylsalicyloyl)Piperazine—(route:mixed anhydride)

(Scheme A—Product V)

Dissolve 9.4 g of acetylsalicylic acid (0.052 moles) and anhydrous triethylamine (5.3 g; 7.3 ml; 0.052 moles) in an anhydrous ketone, preferably represented by acetone (100 ml). Cool the solution below 0° C., and then add slowly ethyl chlorocarbonate (5.5 g; 5.0 ml; 0.052 moles) diluted with a ketone, represented preferably by acetone (10 ml), whilst stirring and cooling, so as to form the compound of formula (III) wherein R represents $-C_2H_5$. After shaking, and cooling constantly, add in a single aliquot anhydrous piperazine base (2.1 g; 0.025 moles). Shake for 2-5 hours allowing the temperature of the reaction mixture to rise spontaneously up to room temperature. Remove by filtration all formed triethylamine hydrochloride, and pour the filtrate into distilled water. Collect the separate solid, wash it with water and crystallize from ethanol.

The resulting product is endowed with the same chemical and physicochemical characteristics as those specified in Example 1.

EXAMPLE 3

1,4-bis(3-(Acetylsalicyloyloxy)Propyl)Piperazine (Formula I: X=O—CH$_2$CH$_2$CH$_2$—)

Dissolve 1,4-bis-(3-hydroxypropyl)piperazine (10.1 g; 0.05 moles) in anhydrous tetrahydrofuran (200 ml); heat slowly (30°–40°), and slowly add thereafter acetylsalicyloyl chloride (20 g; 0.1 moles) diluted with anhydrous tetrahydrofuran (50 ml).

Heat the mixture up to the boiling point until the reaction is terminated and thereafter, after allowing the mixture to cool, add anhydrous hydrochloric acid in ethanol to the reaction fluid; concentrate the reaction fluid, allow to stand in a cold environment for a few hours, and filter by pump the raw salt which can be recrystallized from diluted ethanol.

The free base can be obtained from the resulting dihydrochloride, by duly alkalinizing the aqueous solution of the salt with potassium carbonate and extracting thereafter the basic solution with chloroform. The chloroform extracts, pooled, dried ($K_2CO_3$), filtered and evaporated under a reduced pressure, provide a white solid residue that crystallizes from diisopropylether; m.p.83–86° C. (Kofler, not corr.).

For $C_{28}H_{34}N_2O_8$ (526.57)—% found: C 63.72; H 6.66; N 5.21; % calc.: C 63.86; H 6.51; N 5.32.

I.R. (Nujol)

1770 cm$^{-1}$ (stretching $\diagdown\diagup$C=O of the group $CH_3-\overset{\overset{O}{\|}}{C}-O-Ar$)

1730 cm$^{-1}$ (stretching $\diagdown\diagup$C=O of the group $R-\overset{\overset{O}{\|}}{C}-O-(CH_2)_3-$)

N.M.R., δ pertaining to T.M.S. (CDCl$_3$); 1.6–2.8 (multiplet; 22 H)>N—$\underline{CH_2}$—$\underline{CH_2}$—$\underline{CH_2}$—O, piperazine H; $CH_3$—COOAr distinguishable as singlet at 2.30 δ; 4.27 (triplet; 4 H)>N—CH$_2$—CH$_2$—$\underline{CH_2}$—O—CO; 6.93—7.70 (multiplet; 6 H) aromatic H in meta and para (*); 7.98 (double doublet; 2 H) aromatic H in ortho (**).

EXAMPLE 4

1,4-bis(2-(Acetylsalicyloyloxy)Propyl)Piperazine (Formula I; X = $-O-\underset{\underset{CH_3}{|}}{CH}-CH_2-$)

Dissolve acetylsalicylic anhydride (17.1 g; 0.05 moles) in an apolar organic solvent represented for example by ethyl acetate; add 1,4-bis-(2-hydroxypropyl)piperazine (5.06 g; 0.025 moles) to the solution, and heat up to the boiling point until the reaction is completed. After cooling at room temperature, wash the reaction mixture with a 5 percent aqueous solution of potassium carbonate, and then with water. Anhydrify the organic phase ($K_2CO_3$), filter, and treat it with anhydrous hydrochloric acid dissolved in diethylether causing by this procedure the precipitation of the raw product that, after collection and drying, can be recrystallized from a low molecular weight alcohol.

M.p. 173°–175° C. (kofler, not corr.).

For $C_{28}H_{36}Cl_2N_2O_8$(599.51)—% found: C 55.90; H 6.25; N 4.48- % calc.: C 56.10; H 6.05; N 4.67.

Argentimetric Assay 100.3%.

I.R. (Nujol)

1770 cm$^{-1}$ (stretching of $\backslash$C=O of the group $CH_3-\overset{\overset{O}{\|}}{C}-O-Ar$)

1730 cm$^{-1}$ (stretching of $\backslash$C=O of the group $Ar-\overset{\overset{O}{\|}}{C}-O-\underset{\underset{CH_3}{|}}{CH}-$)

N.M.R.

δ relative to T.M.S. (CDCl$_3$)

1.25 (doublet, 6H) $-CH_2CH-$
$\quad\quad\quad\quad\quad\quad\quad\quad |$
$\quad\quad\quad\quad\quad\quad\quad\quad CH_3$ 1.9–3.0 (multiplet, 18H) piperazine H +

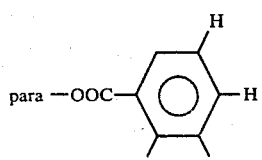 N—CH$_2$—CH$_3$—COOAr distinguishable as singlet at 2.30

5.0–5.5. (multiplet, 2H) $-CH_2-\underset{\underset{CH_3}{|}}{CH}-O-$ 6.93–7.70 (multiplet, 6H) aromatic H in meta and

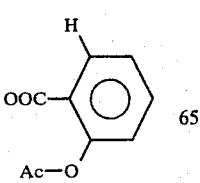

7.97 (double doublet, 2H) - aromatic H in ortho OOC—

EXAMPLE 5

1,4-bis(2-(Acetylsalicyloyloxy)-1-Methyl-Ethyl)Piperazine (Formula I: X = $-O-CH_2-\underset{\underset{CH_3}{|}}{CH}-$)

Operate according to the procedure described in Example 3 starting from 1,4-bis-(2-hydroxy-1-methylethyl)piperazine (5.0 g; 0.25 moles). Crystallize the product from ethanol or from aqueous ethanol (mp 203°–205° C., Kofler, not corrected).

For $C_{28}H_{36}Cl_2N_2O_8$(599,51)—% found: C 56.22; H 5.85; N 4.76—% calc.: C 56.10; H 6.05; N 4.67.

Argentimetric Assay 99.5%.

I.R.

1770 cm$^{-1}$ (stretching $\backslash$C=O of the group $CH_3-\overset{\overset{O}{\|}}{C}-O-Ar$)

1730 cm$^{-1}$ (stretching $\backslash$C=O of the group $Ar-\overset{\overset{O}{\|}}{C}-O-CH_2-$)

N.M.R.

δ relative to T.M.S. (CDC$_3$)

1.08 (doublet, 6H) $\backslash$N—CH—
$\quad\quad\quad\quad\quad\quad\quad / \quad\quad |$
$\quad\quad\quad\quad\quad\quad\quad\quad\quad CH_3$ 2.33 (singlet, 6H) $CH_3-COO-$ 2.43–3.23 (multiplet, 10H) piperazine H, 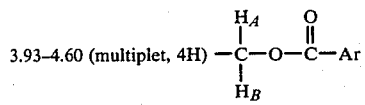

3.93–4.60 (multiplet, 4H) $-\underset{\underset{H_B}{|}}{\overset{\overset{H_A}{|}}{C}}-O-\overset{\overset{O}{\|}}{C}-Ar$ 6.97–7.70 (multiplet, 6H) aromatic H in meta and

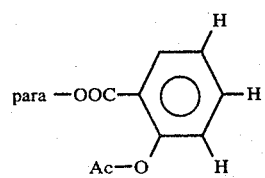

8.00 (double doublet, 2H) aromatic H in ortho OOC—

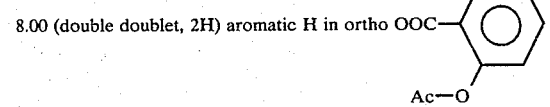

EXAMPLE 6

1,4-bis(2'-(Acetylsalicyloyloxy)Ethyl)Piperazine (Formula I: X=—O—CH₂—CH₂—) (route: acid chloride)

Dissolve 1,4-bis-(2'-hydroxyethyl)piperazine dihydrochloride (mp 200°-202° dec.) (6.0 g; 0.024 moles) and anhydrous triethylamine base (4.9 g; 6.7 ml; 0.048 moles) in anhydrous tetrahydrofuran. Heat the mixture for 30 minutes under reflux, cool at 40° C. and, while stirring, add acetylsalicyloyl chloride (9.53 g; 0.048 moles) diluted with anhydrous tetrahydrofuran (40 ml). Heat again under reflux keeping boiling temperature for 20 hours approximately. Add anhydrous hydrochloric acid dissolved in ethanol. Transfer the reaction mixture for some hours to a cold environment in order to complete crystallization; collect the solid aliquot, wash it accurately on the filter with tetrahydrofuran, and finally recrystallize the product from ethanol (mp 197°-198° C., Kofler not corrected).

For $C_{26}H_{32}Cl_2N_2O_8$(571.47)—% found: C 54.76; H 5.77; N 5.02—% calc.: C 54.65; H 5.64; N 4.90.

Argentimetric Assay 99.6%.

I.R.

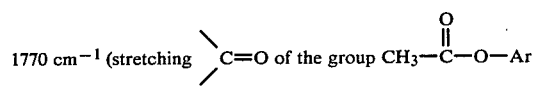

1770 cm⁻¹ (stretching C=O of the group CH₃—C—O—Ar

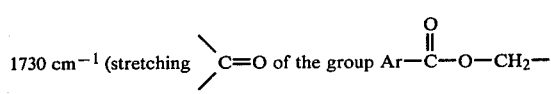

1730 cm⁻¹ (stretching C=O of the group Ar—C—O—CH₂—

EXAMPLE 7

1,4-bis-(2'-(Acetylsalicyloyloxy)Ethyl)Piperazine (Formula I: X=O—CH₂CH₂—) (route: symmetrical anhydride)

A mixture of 1,4-bis(2-hydroxyethyl)piperazine anhydrous base (8.7 g; 0.05 moles) and acetylsalicylic anhydride (34.3 g; 0.1 moles) in tetrahydrofuran is boiled under reflux until an examination with TLC (Merck F₂₅₄ silica gel plates—eluent BuOH, EtOH, CH₃CO₂H, H₂O—60:20:40:30—UV light detection 254 nm) signals that the reaction is completed (over 10 hours).

Evaporate the solvent under a reduced pressure, take up the residue with chloroform, wash the organic solution with 5 percent aqueous potassium carbonate solution, dry (K₂CO₃), and evaporate to dryness under reduced pressure. The oily residue solidifies when allowed to stand in a cold environment. Purify this residue by crystallization from a low molecular weight alcohol, such as ethanol (mp 92°-93° C., not corrected).

For $C_{26}H_{30}N_2O_8$(499,54)—% found: C 62,57; H 6,02; N 5,48 % calc.: C 62.64; H 6.06; N 5.62.

N.M.R.

δ relative to T.M.S. (CDCl₃)

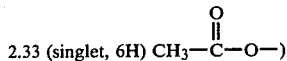

2.33 (singlet, 6H) CH₃—C—O—

2.45–2.90 (multiplet, 12H) piperazine H,

-continued
N.M.R.

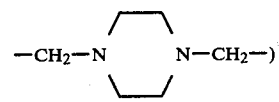

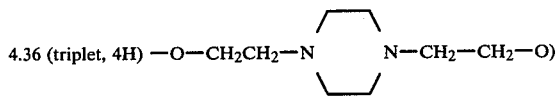

4.36 (triplet, 4H) —O—CH₂CH₂—N    N—CH₂—CH₂—O)

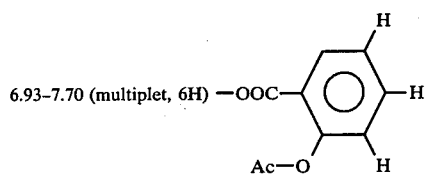

6.93–7.70 (multiplet, 6H) —OOC—

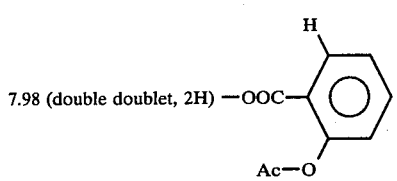

7.98 (double doublet, 2H) —OOC—

EXAMPLE 8

1,4-bis(2'-(Acetylsalicyloyloxy)Ethyl)Piperazine (Formula I; X=—O—CH₂CH₂—) (route: mixed anhydride)

Dissolve acetylsalicylic acid (10 g; 0.055 moles) in acetone (100 ml), and add anhydrous triethylamine base (5.6 g; 0.055 moles). Cool the mixture under 0° C. and then, while stirring, add slowly isobutylchlorocarbonate (7.5 g; 0.055 moles), so as to form the compound of formula (VII) where R represents —CH₂CH(CH₃)₂.

Shake for 30 minutes approximately, always cooling, and add thereafter, once and for all, anhydrous 1,4-bis(2-hydroxyethyl)piperazine base (4.36 g, 0.0025 moles), diluted with the ketone (50 ml). Keep stirring, cooling for 30 minutes approximately, and allow thereafter temperature to attain spontaneously room temperature, still shaking for some hours until the reaction is completed. Filter the separated triethylamine hydrochloride, and remove the solvent by distillation under a reduced pressure. Dissolve the residue with chloroform; wash the chloroform solution with water, with 5 percent potassium carbonate, and again with water. Finally, dry (K₂CO₃), and evaporate the solvent. Dissolve the residue in hot ethanol and dissolve separately maleic acid in hot absolute ethanol. While stirring, mix the two warm solutions causing consequently the crystallization of the acid dimaleate of the base, 1,4-bis-(2'-acetylsalicyloyloxyethyl)piperazine; this acid dimaleate salt can be further purified by crystallization from absolute ethanol (mp 156°-158° C., not corrected). Analogously, the corresponding tartrate (mp 144°-147° C., not corrected, from ethanol); sulphate (mp 205°-207° C., not corrected, from aqueous ethanol), and citrate (mp 131°-133° C., not corrected, from absolute ethanol) were prepared from the resulting base.

EXAMPLE 9

1,4-bis(1'-Ethyl-2'-(Acetylsalicyloyloxy)Ethyl)Piperazine (Formula I; X = —O—CH$_2$—CH—)
                              |
                              C$_2$H$_5$ The product was obtained using acetylsalicyloyl chloride and a similar procedure to that specified in Example 5. The free base crystallizes from a low molecular weight alcohol or from diisopropyl ether.

M.p. 84°–89° C. (Kofler, not corr.).

For C$_{30}$H$_{40}$Cl$_2$O$_8$ (627.55)—% found: C 57.62; H 6.66; N 4.50—% calc.: C 57.41; H 6.43; N 4.46.

Argentimetric Assay 99.7%.

I.R.

1770 cm$^{-1}$ (stretching \C=O of the group CH$_3$—C(=O)—O—Ar)

1730 cm$^{-1}$ (stretching \C=O of the group Ar—C(=O)—O—CH$_2$—)

N.M.R.

δ relative to T.M.S. (CDCl$_3$)

0.7–1.8 (multiplet, 10H) \N—CH—CH$_2$—
                                |
                                CH$_2$—CH$_3$ 2.30 (singlet, 6H) CH$_3$—COO—

2.4–3.0 (multiplet, 10H) × piperazine H +

—CH—N(piperazine)N—CH—

3.9–4.6 (multiplet, 4H) \N—CH—C(H$_A$)(H$_B$)—O—
                                  |
                                  C$_2$H$_5$ 6.97–7.73 (multiplet, 6H) aromatic H in meta and para —OOC-(ring)-H, Ac—O 7.97 (double doublet, 2H) aromatic H in ortho OOC-(ring), Ac—O

EXAMPLE 10

1,4-bis(2'-(Acetylsalicyloyloxy)Ethyl)Piperazine (Formula I; X=—O—CH$_2$CH$_2$—) (route: SCHEME B)

To an apolar anhydrous solvent, with boiling temperature higher than 100° C. (100 ml) is added 2'-bromoethylacetylsalicylate (14.4 g, 0.05 moles), anhydrous potassium carbonate (7.0 g, 0.05 moles approximately), potassium iodide (0.9 g, 5 moles approximately), and piperazine anhydrous base (2.2 g, 0.025 moles). Heat the mixture up to the boiling point and maintain it at the boiling point until termination of the reaction. After cooling, filter the reaction mixture, and remove the solvent under a reduced pressure. Dissolve the residue with ethyl acetate. Wash the organic solution with 5 percent aqueous potassium carbonate, then with water, anhydrify thereafter (K$_2$CO$_3$), filter and treat the filtrate with hydrochloric acid dissolved in diethyl ether, causing consequent precipitation of the dehydrochloride m.p. 197°–198° C. (from ethanol), identical to the product of Example 6.

We claim:

1. A compound of the formula (structure: Ar—C(=O)—X—N(piperazine)N—X—C(=O)—Ar, with O—C(=O)—CH$_3$ substituents)

wherein X represents a direct linkage between the carbon and nitrogen atoms or a linear or branched oxyalkyl group having 2–4 carbon atoms linked through its oxygen atom to the nitrogen atom, and the pharmaceutically acceptable salts thereof.

2. A compound according to claim 1 in which X constitutes a direct linkage between the carbon and nitrogen atoms.

3. A compound according to claim 1 in which X is 2-oxyethyl.

4. A compound according to claim 1 in which X is 3-oxypropyl.

5. A compound according to claim 1 in which X is 2-oxypropyl.

6. A compound according to claim 1 in which X is 2-oxy-1-methyl ethyl.

7. A compound according to claim 1 in which X is 2-oxy-1-ethyl ethyl.

8. A compound of the formula (I)

(structure: Ar—C(=O)—X—N(piperazine)N—X—C(=O)—Ar, with O—C(=O)—CH$_3$ substituents)

wherein X represents a linear or branched alkylene group having 2–4 carbon atoms, and the pharmaceutically acceptable salts thereof.

9. A pharmaceutical composition having antipyretic, analgesic, anti-inflammatory and antihistaminic activities suitable for oral, parenteral, rectal or topical administration containing, as the active ingredient, and antipyretic, analgesic, anti-inflammatory and antihistaminic effective amount of a compound according to claim 1.

* * * * *